(12) United States Patent
Haik, Jr.

(10) Patent No.: US 6,727,285 B1
(45) Date of Patent: Apr. 27, 2004

(54) USE OF D-ARGININE AND/OR L-ARGININE TO PROTECT THE AMINO GROUPS OF BIOLOGICAL SUBSTANCES FROM DAMAGE, INACTIVATION, OR MODIFICATION BY TOXIC CARBONYLS AND/OR DICARBONYLS

(76) Inventor: George M. Haik, Jr., 296 Audubon Blvd., New Orleans, LA (US) 70125

( * ) Notice: Subject to any disclaimer, the term of this patent is extended or adjusted under 35 U.S.C. 154(b) by 870 days.

(21) Appl. No.: 09/079,329

(22) Filed: May 14, 1998

Related U.S. Application Data

(60) Provisional application No. 60/059,420, filed on Jul. 31, 1997, provisional application No. 60/046,430, filed on May 14, 1997, and provisional application No. 60/006,304, filed on Nov. 7, 1995.

(51) Int. Cl.$^7$ .................. A61K 38/00; A61K 31/198

(52) U.S. Cl. ........................................ 514/565; 514/12

(58) Field of Search .......................................... 514/631

(56) References Cited

PUBLICATIONS

Database CaPlus, DN 91:1812. Kadowaki, H. et al. Int. J. Biochem. (1979), 10(4), 303–10 Apr. 1979.*
Khaidar, A. et al. Circulation, 90, 479–483, Feb. 1979.*
Lo et al. J. Biol. Chemistry, 269, 32299–32305, Dec. 1994.*
Database CAPLUS, AN 489354. Selwood, T. et al. Biochem. Soc. Trans. 21, 170S, Feb. 1993.*

* cited by examiner

*Primary Examiner*—Michael Borin
(74) *Attorney, Agent, or Firm*—Garvey, Smith, Nehrbass & Doody, L.L.C.; Seth M. Nehrbass

(57) ABSTRACT

A method of blocking dicarbonyls and carbonyls in vitro and in vivo includes using an effective quanity of an L- or D-arginine, substituted arginine, modified arginine or arginine-containing blocking agent. The method can, for example, include blocking toxic dicarbonyls and carbonyls in a patient suffering from a condition associated with toxic carbonyls and/or dicarbonyls, by administering to the patient a therapeutically effective dose of an L- or D-arginine, substituted arginine, modified arginine or arginine-containing blocking agent.

8 Claims, 3 Drawing Sheets

FIG. 7 Human Proinsulin

US 6,727,285 B1

USE OF D-ARGININE AND/OR L-ARGININE TO PROTECT THE AMINO GROUPS OF BIOLOGICAL SUBSTANCES FROM DAMAGE, INACTIVATION, OR MODIFICATION BY TOXIC CARBONYLS AND/OR DICARBONYLS

CROSS-REFERENCE TO RELATED APPLICATIONS

Hereby incorporated by reference are my co-pending U.S. patent application Ser. No. 08/848,414, filed May 7, 1997, which is a continuation-in-part application of co-pending U.S. patent application Ser. No. 08/745,060, filed Nov. 7, 1996, and of International Patent Application No. PCT/US96/17821, filed Nov. 7, 1996, all incorporated herein by reference.

My U.S. Provisional Patent Application Ser. No. 60/006,304, filed Nov. 7, 1995, is hereby incorporated by reference.

My U.S. Provisional Patent Application Ser. No. 60/046,430, filed May 14, 1997, is hereby incorporated by reference. Priority of that application is hereby claimed.

My U.S. Provisional Patent Application Ser. No. 60/059,420, filed Jul. 31, 1997, is hereby incorporated by reference. Priority of that application is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method for removing or blocking toxic carbonyl containing compounds and/or dicarbonyl containing compounds to prevent them from otherwise binding to and/or cross-linking proteins, forming protein adducts and/or cross-linked complexes, denaturing proteins, disrupting protein structure and/or function, and/or from causing disease states produced by or associated with carbonyl- and/or dicarbonyl-induced protein complexes. As is shown herein, the present invention is also applicable when applied in vitro, for example, to bovine serum albumin, but not limited to that usage. More particularly, the present invention relates to a method of using D- and/or L-arginine, or substituted or modified arginine, or arginine-containing compounds to remove or block toxic carbonyls and/or dicarbonyls, for example in vivo. Still more particularly, the present invention relates to a method of treating disease states which are associated with levels of toxic carbonyls and/or dicarbonyls in vivo, such as diabetes mellitus and acute chemical poisoning, by removing or blocking toxic carbonyls and/or dicarbonyls with the therapeutic administration of L- and/or D-arginine; for example, one embodiment of the present invention relates to the treatment of diabetes mellitus by reducing the in vivo level of toxic dicarbonyl-containing methylgloxal and related toxic metabolites of sugar in a patient by administering L- and/or D-arginine to a patient.

The present invention relates also to a method for removing, blocking, or scavenging dicarbonyls and carbonyls in vitro. More particularly, the present invention relates to a method of using D-arginine and/or L-arginine, or arginine-containing compounds to remove (scavenge or attach to) or block carbonyls or dicarbonyls.

2. General Background of the Invention

Reactive carbonyl groups, for example in vivo are toxic by, inter alia, reacting with native proteins to form adducts and/or cross-linked complexes. This process can inactivate important proteins as well as form unwanted protein complexes in vivo. Indeed, a number of ailments are believed to be caused by the accumulation in vivo, and subsequent reaction of toxic carbonyls and/or dicarbonyls and toxic carbonyls and/or dicarbonyl-containing compounds with native compounds such as proteins. For example, it is believed that at least some complications associated with diabetes mellitus, such as, for example, cataracts and kidney problems, are related to the accumulation in vivo, and reaction of toxic dicarbonyl-containing compounds that are sugar-derived, such as, for example, but not limited to, methylglyoxal, glyoxal, deoxyglucosone and chemicals of similar structure. It is believed that, for example, in diabetes mellitus, high blood glucose levels can lead to high levels of methylglyoxal. The methylglyoxal can then, via its reactive dicarbonyl group, react with native proteins leading to, inter alia, unwanted protein-methylglyoxal adducts and cross-linked proteinaceous complexes. These complexes can then be responsible for such symptoms of diabetes mellitus as cataracts and kidney problems.

The ocular structures of higher vertebrates vary structurally and chemically from those of humans. For example, the human eye lacks the tapetum lucidum of many higher vertebrates, for example the deer. The human sclera contains no bones as in birds. Human aqueous humor does not coagulate as in the rabbit. The human retina contains color receptor pigments lacking in the dog. Prior to the publication of the inventor's exhaustive biochemical and enzymatic study of the human eye no one had isolated methylglyoxal, glyoxalase I and glyoxalase II from the human lens (Haik et al. 1994, which is incorporated herein by reference).

Whether diabetic or not the human lens is never vascularized and is completely dependent on anaerobic glycolysis. Accordingly, both diabetics and non-diabetics produce levels of methylglyoxal in the human lens many times higher than normal blood levels. Our experiments with bovine serum albumin have shown that methylglyoxal has the ability to produce solid yellow gel formation from liquid proteins. The inventor attributes this at least primarily, and not intending to be bound by theory, to imine bond formation and the cross-linking of proteins.

As discussed in more detail below, the inventor has discovered that one can block methylglyoxal-induced gel formation of liquid bovine serum albumin by pretreatment with D-arginine or L-arginine in the free base or hydrochloride form. The inventor believes, but does not intend to be limited by any particular theory, that a process involving protein cross-linking by methylglyoxal (and perhaps to a lesser degree by glyoxal and other dicarbonyls) can produce rapid cataract formation in diabetics and relatively slower senile cataracts formation in non-diabetics over a period of years. Larger amounts of methylglyoxal would be expected to be produced from higher concentrations of the substrate glucose, however, free methylglyoxal levels are rapidly diminished by attachment to available proteins and amino acids or detoxified via the glutathione-dependent glyoxalase system. This is especially important since levels of reduced glutathione diminish with oxidative stress and the aging of tissues.

Increased levels of toxic carbonyl-containing compounds associated with high glucose levels, such as methylglyoxal, can also form adducts in the blood which can lead to kidney problems. Additionally, occupational or accidental exposure to toxic carbonyl-containing compounds can cause any number of medical complications associated with the formation of protein adducts within the body such as, for example, cataracts, arthritis, kidney, lung and circulation problems (not to exclude circulation problems in the retina referred to as diabetic retinopathy, and not to exclude vasculopathy elsewhere in the extremities) and so forth. Finally, it is believed that at least some of the physiological changes associated with aging, such as senile cataracts, are related to adduct formation caused by such toxic agents as toxic dicarbonyls.

It is therefore desirous to devise a method of removing and/or blocking toxic carbonyls and/or dicarbonyls from, for example in vivo environments before they react with native tissues to form adducts and/or detrimental cross-linked complexes. However, prior to the present invention, such a method was not known, making adduct formation and cross-linking formation from toxic carbonyls and/or dicarbonyls a problematic clinical and/or aging phenomenon.

The present invention provides a method for removing toxic carbonyls and/or dicarbonyls from environments, for example in vivo environments, before they react with tissues to form adducts and/or detrimental cross-linked complexes, thereby providing a method for eliminating or reducing the detrimental effects caused, for example in vivo, by toxic dicarbonyls.

The present invention recognizes that both L- and D-arginine are reactive with toxic carbonyls and dicarbonyls in such a manner that the presence of D- and/or L-arginine can react with toxic carbonyls and dicarbonyls in order to block and/or remove them before they can react with other compounds, such as native proteins. The present invention further recognizes that L- and/or D-arginine can, for example in vivo, effectively compete with native "target" compounds, such as proteins, for binding to any toxic dicarbonyls and carbonyls that might be present, thereby providing a method for blocking and/or removing toxic carbonyls and/or dicarbonyls from an environment before the dicarbonyls and/or carbonyls can react with native tissues and cause damage.

The present invention further recognizes that in addition to physiologically active L-arginine, importantly one can also use non-naturally occurring D-arginine with the instant invention. The use of D-arginine to block and/or remove toxic dicarbonyls and/or carbonyls from, for example in vivo environments provides a non-physiologically reactive substance with which to block and/or remove toxic dicarbonyls and/or carbonyls. This can be of great value as it provides a means of administering a water soluble and excretable scavenger that is not physiologically active other than to act in the blocking/scavenging manner of the present invention.

BRIEF SUMMARY OF THE INVENTION

The method of the present invention solves the problems confronted in the art in a simple and straightforward manner. The present invention recognizes that D- and L-arginine can, for example in vivo, reduce the level of toxic carbonyls and/or dicarbonyls and thereby reduce or prevent adduct formation and cross-linking with native tissues which would otherwise be caused by the presence of toxic dicarbonyls and/or carbonyls in a living body. What is provided therefore is a method which utilizes arginine, and/or substituted or modified arginine, to preferentially and chemically react with toxic carbonyls and dicarbonyls, preferably in vivo, to thereby remove them before they react with native tissues to form detrimental adducts and/or cross-linked complexes. This method can reduce the level, and/or block toxic carbonyls and dicarbonyls in a living body and thereby reduce the damaging effects caused by cross-linking and/or adduct formation of carbonyls with native tissues.

It is further recognized and an aspect of the present invention that in addition to physiologically active L-arginine, importantly one can also use non-naturally occurring D-arginine to block and/or remove toxic dicarbonyls and/or carbonyls from, for example in vivo environments. The use of D-arginine importantly provides a non-physiologically reactive substance with which to block and/or remove toxic dicarbonyls and/or carbonyls from a living system.

It is an object therefore of the present invention to provide a method of removing toxic carbonyls and/or dicarbonyls, for example from a living body by administering a therapeutically effective dose of L- and/or D-arginine or an arginine-containing compound to a living body, the arginine thereby chemically reacting with the carbonyl group and preventing its reaction with native tissues.

It is a further object of the present invention to provide a method of preventing, alleviating or reducing complications associated with toxic carbonyls and/or dicarbonyls forming adducts and/or cross-links with native tissues by the therapeutic administration of L- and/or D-arginine or arginine-containing compounds to prevent such complex formation.

It is a further object of the present invention to provide a method of treating, for example, complications arising from cross-linking and/or adduct formation caused by toxic carbonyls and/or dicarbonyl-containing sugar metabolites such as methylglyoxal in diseases such as diabetes mellitus, by administering a therapeutically effective dose of L- and/or D-arginine, or substituted or modified arginine, or arginine-containing compounds to a living body.

Further, it is an object of the present invention to utilize non-naturally occurring and non-physiologically reactive D-arginine as the toxic dicarbonyl and/or carbonyl blocking and/or reacting agent of the present invention.

BRIEF DESCRIPTION OF THE DRAWINGS

For a further understanding of the nature, objects, and advantages of the present invention, reference should be had to the following detailed description, read in conjunction with the following drawings, and wherein:

FIG. 7 shows schematically proinsulin structure.

Figure 2:
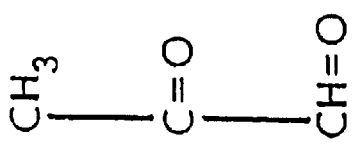
FIG. 2 shows the structure of methylglyoxal, a toxic dicarbonyl metabolite of, for example, glucose and a target of the blocker of the instant invention, arginine (L-arginine, D-arginine, and any racemic mixture thereof), substituted or modified arginine (Levorotary form, Dextrorotary form, or any racemic mixture), or arginine-like molecules in L-form, D-form or any stereoisometric combination.

Table 1 shows a representative but not inclusive list of dicarbonyl structures that can act as "targets" for the arginine blockers of the present invention;

Table 2 shows an illustrative list of possible types of arginine, substituted arginine and/or modified arginine blockers of the present invention including complexes such as polypeptides;

Table 3 shows biochemical pathways related to sugar metabolism, diabetes mellitus and the production of the toxic dicarbonyl compound methylglyoxal including the roles of the enzymes glyoxalase I and II enzymes; additionally, it shows a role for glutathione (GSH) in the function of glyoxalase I;

Table 4 shows the results of Example 1;

Table 5 shows the results of Example 2;

Table 6 shows the results of Example 3; and

Table 7 shows the effect of pH changes on the reaction of methylglyoxal with bovine serum albumin.

DETAILED DESCRIPTION OF THE INVENTION

The present invention recognizes that both L- and D-arginine, and stereoisomer combinations of arginine, as well as substituted and modified forms, can be used to block and/or inactivate toxic carbonyls and/or dicarbonyls that would otherwise in vivo (and in vitro) react with native proteins (aminated compounds) to form detrimental adducts and/or cross-linked complexes. The instant invention recognizes that both L-(levorotary) and D-(dextrorotary) stereoisomers (including modified and substituted forms) of the amino acid arginine are active in this capacity. This means that both naturally occurring and physiologically active L-arginine and non-naturally occurring and physiologically inactive D-arginine can be used in the method of the present invention.

It is important, and a preferred embodiment of the present invention, that D-arginine can be used as the blocker or "scavenger" of the present invention as many advantages may be presented by using D- over L-arginine. For example, because D-arginine has no other known use in living systems and is not recognized by known enzymes or other biologic machinery, it is possible to practice the present invention by administering a blocking specific blocker that is not otherwise biologically active. This can allow, for example, the blocking of toxic carbonyls and dicarbonyls in a living being without otherwise affecting the living body being medicated, i.e., the blocking agent/medicant would have no other biological function. This could, for example, greatly reduce the risk of side effects from the practice of the present invention. Further, while D-arginine is not biologically active, other than as a blocking agent in the practice of this invention, nonetheless it is water soluble and therefore excretable. Hence, in the practice of the instant invention using D-arginine, for example, administration of the blocker is not toxic due either to biological activity or biological accumulation, for example.

Specifically, the present invention is demonstrated both in vitro and in vivo and it is shown that, in fact, both D- and L-arginine can act to block and inactivate toxic dicarbonyls before they can form physiologically detrimental complexes. At least one disease state, diabetes mellitus, is studied in detail in order to provide one example of the beneficial use of the present invention.

Figure 1:
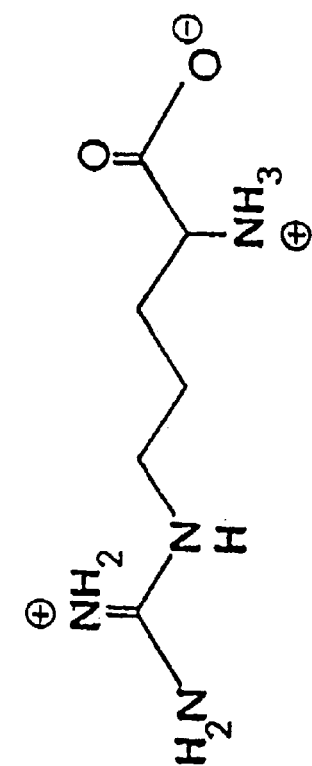
FIG. 1 shows the structure of arginine; arginine may be modified and/or substituted in keeping with the practice of the present invention.

Arginine (2-amino-5-guanidovaleric acid) (FIG. 1) is a water soluble dibasic amino acid with a molecular weight of 174.20 containing a reactive guanidino grouping. The L form of arginine occurs in mammalian systems and is enzymatically reactive, whereas the D form of arginine does not occur naturally in mammalian systems and is not enzymatically reactive. Both are especially well suited as scavengers and protectants against the reactive dicarbonyls of methylglyoxal, glyoxal, deoxyglucosone and similar compounds of the following structures (and see FIG. 2 and Table 1):

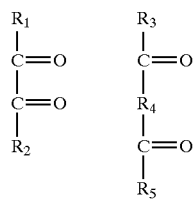

R can be any substitution group including, but not limited to H, CH, $CH_2$, $CH_3$, C=O, COOH, $CNH_2$, $NH_2$, $CH_2CH_3$, COH, CHR, $CH_2R_6$, $CH_2CH_2CH_3$, $CHR_6CH_2R_6$, $C_nH_x$, and all combinations thereof, where $R_6$ can be any R without $R_6$ in it (the second structure represents compounds of lipid metabolism such as malondialdehyde which have been implicated in coronary artery disease); additionally, R can be omitted and $R_4$ cannot be H.

Figure 3:
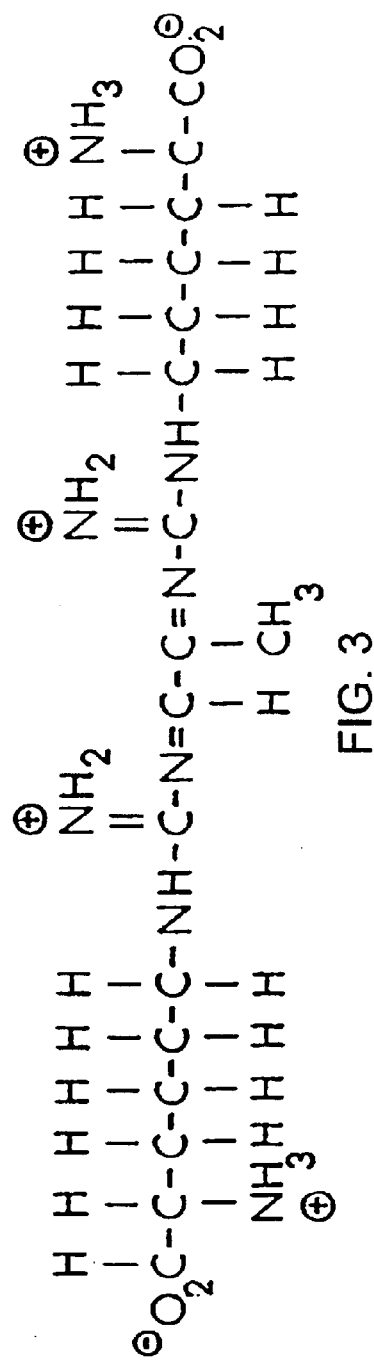
FIG. 3 shows the structure of one possible adduct, a dimer adduct of methylglyoxal-arginine, formed by a blocking reaction of the present invention, the reaction of arginine with methylgyloxal.
Figure 4:
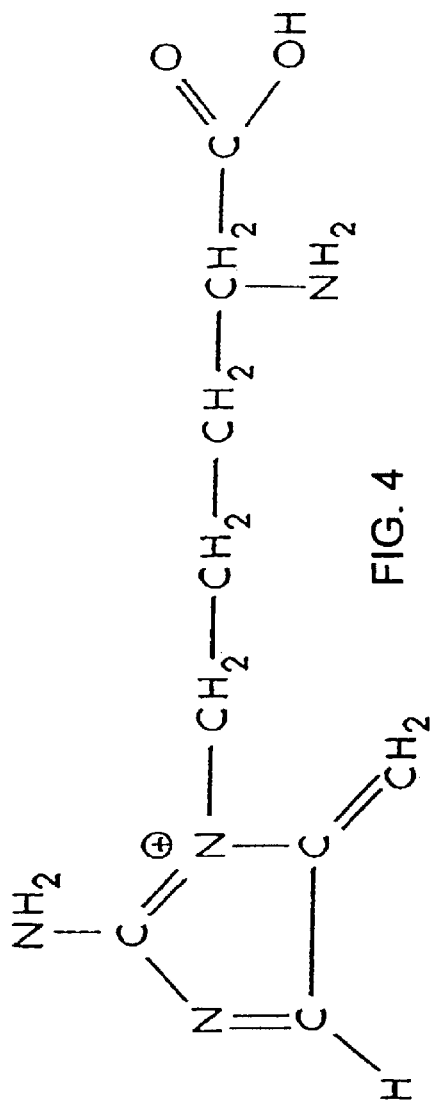
FIG. 4 shows the structure of one possible adduct, a methylglyoxal-arginine adduct, formed by a blocking reaction of the present invention, the reaction of arginine with methylgyloxal.
Figure 5:
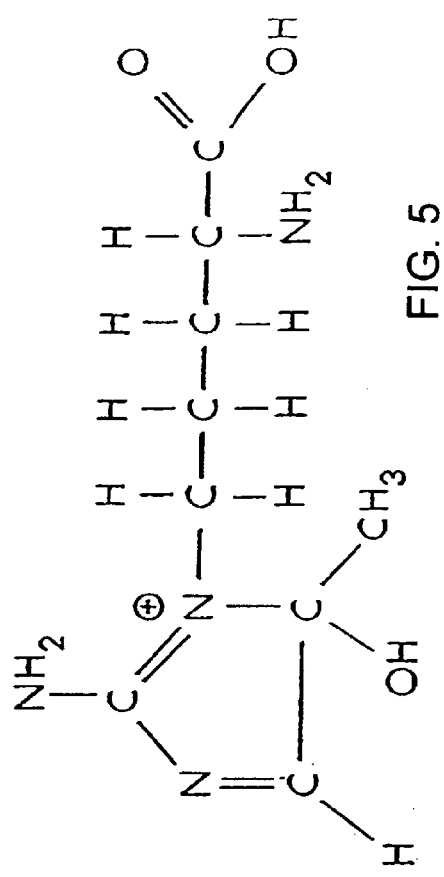
FIG. 5 shows the structure of one possible adduct, a methylglyoxal-arginine adduct, formed by a blocking reaction of the present invention, the reaction of arginine with methylgyloxal.

In the present invention, arginine can react with any of the above-identified compounds forming, for example, the products shown in FIGS. 3–5. In addition, arginine or other toxic carbonyl and/or dicarbonyl blockers of the present invention can react with any chemical structure that is reactive with the group or with any compound containing any such reactive structure. This can include, for example but not limited to, the following groups and compounds containing the following groups: carbonyls, dicarbonyls, deoxyglucosone, methylglyoxal, glyoxal, malonic acid aldehyde, malonidialdehyde, formaldehyde, gluteraldehyde and other aldehydes (see also Table 1).

Further by example and not in a limiting sense, in the present invention, the carbonyl and/or dicarbonyl blocker arginine may be present as free L- and/or D- arginine, or as free base forms or salts thereof, or may be present as part of a larger complex such as, for example, a peptide, or, for example, be administered as a prodrug form wherein the active arginine is specifically delivered or uncovered in vivo. The blocker may also be supplied in a precursor form such as, for example, by supplying precursors of L-arginine biosynthesis such that in vivo L-arginine is produced. Table 2 shows illustrative, but not limiting, types of substituted arginine and arginine-derived blockers and scavengers of dicarbonyls (and carbonyls) of the present invention.

It is important to note that the present invention involves the use of any arginine, modified or substituted arginine or arginine-like molecule (such as, for example but not limited to those structures shown in Table 2) that is reactive with any appropriate target such as, for example, carbonyls and dicarbonyls. This includes modifications and/or substitutions of arginine that, for example, would make the chemical group more reactive with dicarbonyls and/or the inclusion of the arginine or arginine-like group into complexes such as polypeptides and/or prodrugs (see, for example, Table 2).

Of further note, the reactive "target" group to be blocked by the arginine, modified or substituted arginine or arginine-like blocker of the present invention can include toxic dicarbonyl groups, dicarbonyl-containing molecules, as well as simple aldehydes and the like such as formaldehyde and any other chemical group that is reactive with arginine and arginine-like molecules.

Nothing in the prior art is known that anticipates or renders the present invention obvious. To date there have been published studies of free L-arginine dietary supplements reducing heart collagen accumulation in diabetic mice (Khaidar, A., et. al.). Also, L-arginine has been shown to protect against neurotoxicity induced by 1-methyl4-phenylpyridinium ion (Santiago, M., et.al.). Also, it has been shown that L-arginine, but not D-arginine, is acted upon enzymatically by several isoforms of nitric oxide synthetase to produce nitric oxide (Morikawa, E., et.al.). However, the use of arginine as a blocker of toxic dicarbonyls has not been addressed by the prior art. Further, there is no published prior art regarding any beneficial effect of D-arginine.

For example, the toxic carbonyl and dicarbonyl blockers of the present invention can be used in cases such as, but not limited to the treatment of toxic exposure to, for example but not limited to, aldehydes, ketones and ketoaldehydes.

Additionally, the present invention can be used to treat metabolic medical conditions in which oxidative stress could deplete the body stores of "reduced glutathione" and thus compromise the ability of the glyoxalase enzyme system to detoxify dicarbonyls such as methylglyoxal including such medical conditions as diabetic ketoacidosis, lactic acidosis, metabolic acidosis, respiratory acidosis, uremia, and localized tissue anoxia as produced by the narrowing of blood vessels to a target organ such as the heart, muscle, brain, kidney and so forth (indeed, methygloyal itself can be considered to attack glutathione especially at the cystine moiety of this tripeptide). This includes vascular obstruction by clots and hyperviscosity syndromes, e.g., polycythemia vera rubra, in short, any disease condition that can produce a diminished amount of oxygenated blood to reach a target tissue. Table 1 shows, for example, some representative types of dicarbonyl structures that can be blocked by the practice of the present invention.

FIG. 7 shows schematically proinsulin structure (for the full proinsulin structure see, e.g., Wyngaarden, J. B., and Smith, L. H.; CECIL, TEXTBOOK OF MEDICINE, 16th ed., 1982, pp. 1056 & 1057). The A chain, C-peptide, and B chain of human proinsulin are bound by Arginine-Arginine and Arginine-Lysine segments which are exquisitely susceptible to attack by methylglyoxal. The C-peptide (connecting peptide) is split out of the proinsulin molecule at the position of these segments proteolytically (residual arginines and lysine are removed) in the process of making functional human insulin.

Glucagon is composed of a single strand of 29 amino acids. Glucagon acts to increase adenylate cyclase activity in the liver, increasing hepatic cyclic AMP. This causes the breakdown of glycogen. To an extent glucagon and insulin act as a part of a system of checks and balances of blood glucose. (Wyngaarden, J. B., and Smith, L. H.; CECIL, TEXTBOOK OF MEDICINE, 16th ed., 1982, pp. 1056 & 1057).

Independently both arginine hydrochloride and glucagon administration are used to test the adequacy of production of HGH (human growth hormone) in pituitary disease.

Table A is based on information from pages 132 and 133 of Oser, B. L., ed., HAWK'S PHYSIOLOGICAL CHEMISTRY, 14th ed., 1965.

TABLE A

Approximate % Composition of Selected Animal Proteins

| | collagen* | serum albumin | gamma globulin | insulin | pituitary growth hormone | fibrin and fibrinogen |
|---|---|---|---|---|---|---|
| arginine | 8.6 | 6.0 | 4.8 | 3.1 | 9.1 | 7.8 |
| lysine | 5.0 | 12.7 | 8.1 | 2.5 | 7.1 | 9.2 |
| cystine | 0.1 | 6.5 | 3.1 | 12.5 | 0 | 2.7 |

*derived from cattle hide

Pituitary ablation causes reversal of proliferative diabetic retinopathy, presumably because of the removal of the supply of HGH (human growth hormone) which sustains the abnormal vessels or produces modifications of the HGH structures or activity which sustains the abnormal vessels.

As an example of a preferred embodiment of the present invention, the following discussion concerns the administration of arginine as a blocker of toxic dicarbonyl-containing methylglyoxal, a toxic end-product of sugar metabolism and, as discussed above, a problematic compound in diabetes mellitus.

Methylglyoxal is found in elevated amounts in the blood of diabetics and lesser amounts in the blood of non-diabetics. Methylglyoxal is a toxic ketoaldehyde metabolite of glucose and other sugars formed in the Embden-Meyerhoff and Polyol pathways and via anaerobic glycolysis in normal and diabetic human tissues (Table 3).

Glyoxal was produced by Harries in 1904 from benzene, and methylglyoxal was derived from o-xylene by ozonization by A. A. Levine and A. G. Cole in 1932. Glyoxal has been used by embalmers to plasticize tissues. Nobel Prize laureate, Dr. Albert Szent-Gyorgyi describes the high degree of toxicity of methylglyoxal in his text "The Living State" and postulated a role for it in cell proliferation and cancer. Ruth van Heyningen of Nuffield Laboratory at Oxford identified glyoxalase in the lens of rabbits with radiation-induced cataract in 1954.

In 1976 (unpublished works) the present inventor found that 0.2 cc of 40% methylglyoxal is capable of converting two cc of liquid ovalbumin from liquid to solid gelatin within a matter of hours.

In collaboration with Dr. Paul J. Thornalley of the University of Essex the present inventor has identified both methylglyoxal and the enzymes which detoxify it to lactic acid, glyoxalase I (lactoylglutathione lyase) and glyoxalase II (hydroxyaclyglutathione hydrolase) in the human lens (Haik, et.al). Significantly, at birth, the lens consists of living protein and is normally clear. Clinically significant cataracts develop with aging, diabetes, steroid exposure, radiation, trauma and infection. N. Araki, et. al., have described immunochemical evidence of advanced glycation end products in human lens proteins with positive correlation with aging. However, they did not identify the chemistry involved in the production of these end products. Aldose reductase and sorbitol are implicated as causative in diabetic cataracts in the literature. What has been incompletely defined is the nature of the oxidative process which takes place in cataract formation, and how it results in a lens opacity. The present inventor believes that a unique mechanism of protein cross-linking is involved. Cataract formation is an oxidative process that correlates well with a diminished amount of "reduced glutathione" found in age-related cataracts. "Reduced glutathione" is an antioxidant in normal lenses and is the essential coenzyme of the glyoxalase system. The substrate of the glyoxalase system is methylglyoxal, a toxic metabolite of glucose. It is a keto-aldehyde with 2 very reactive carbonyls. Methylglyoxal binds primarily in human proteins to lysine, cysteine, and arginine sites in the tissue protein. The reaction with lysine and cysteine is reversible, and that with arginine is irreversible.

Several inhibitors of glyoxalase I have been identified including compounds containing the tropolone structure, squaric acid derivatives, aflatoxin B1, and glutathione adducts of benzoquinone and naphthoquinone. These inhibitors have not been identified in the human body. The present invention proposes, but does not intend to be bound by any particular theory, that it is not a primary failure of the glyoxalase system which produces tissue damage and cataracts, but rather an excessive flux of glucose-producing methylglyoxal and other dicarbonyls. In age-related cataracts, lens damage from methylglyoxal and other dicarbonyls may occur at lower concentrations over periods of decades. The present inventor suggests that the process of protein cross-linking which is clinically visible as a cataract is analogous to the protein cross-linking in the vasculature and microvasculature of the circulatory system, kidney, retina, brain, nerve tissues and throughout the human body, especially of diabetics. The clinical ramifications of this are especially well demonstrated in diabetics and patients with ischemic vascular disease. Critical to this theory of imine type cross-linking is the fact that all human proteins irrespective of amino acid sequence contain amine groups capable of reacting with free carbonyls.

Methylglyoxal can cross-link and denature protein and is present in elevated amounts in the blood of diabetics and also found in the human crystalline lens. Additionally, glyoxalase I and II are found ubiquitously in mammalian tissues including the human lens. It is reasonable to consider that an excessive methylglyoxal flux in diabetics can produce damage to structural and functional proteins in diabetes.

Furthermore, lesser amounts of methylglyoxal, over a long period of time, may damage the tissues of the non-diabetic. It is reasonable to consider that i) excessive flux of methylglyoxal and similar dicarbonyls such as glyoxal and 3-deoxyglucosone; and/or ii) failure of the glyoxalase system including, but not limited to diminished amounts of the essential coenzyme of glyoxalase I, reduced glutathione, can produce diabetic tissue damage by the dicarbonyl grouping.

Methylglyoxal is a toxic ketoaldehyde by-product of sugar metabolism and the inventor believes it to be an important cause of cross-linking (not to exclude singular attachment, irregular and regular polymer formation, denaturation of proteins, disruption of protein charge and structure, and loss of enzymatic and hormonal protein function, or its damage and damage to structural proteins and their accumulation in organ structures such as the kidney and its vasculature and basement membranes) of human organ proteins via imine bonding to amino groups especially arginine, cysteine, and lysine. The bonding to arginine is irreversible. Methylglyoxal can be detoxified by glyoxalase I and glyoxalase II in the presence of the antioxidant coenzyme "reduced" glutathione with the resulting product being lactic acid. The present inventor has demonstrated for the first time the presence of methylglyoxal and the presence of both glyoxalase I and glyoxalase II in human lens tissue in two separate studies. Importantly, the amount of the essential antioxidant coenzyme glutathione decreases with age in human lens tissue, and this has been implicated in the development of age-related cataract. Additionally, the present invention shows that L-arginine, as well as D-arginine, is capable of blocking the binding of methylglyoxal to both egg albumin and bovine serum albumin. The levorotary form of most amino acids is the biologically active form. However, in the instant invention, the dextrorotary form of arginine is also capable of scavenging methylglyoxal and preventing binding to bovine serum albumin and ovalbumin. There is no appreciable steric hindrance to this reaction. The $sp^2$ II bonding is available to attack by both compounds (see FIG. 6).

Figure 6:
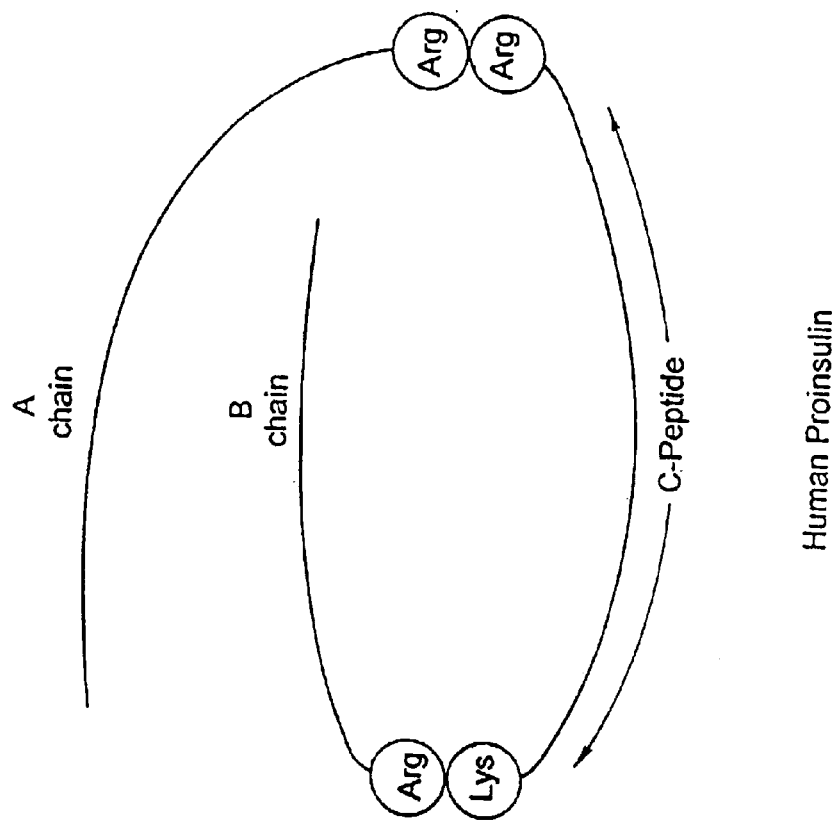
FIG. 6 shows the reactive pi electron clouds above and below the planes of carbonyl groups forming a reactive target site or sites for the blocking arginine of the present invention. Attack on the $sp^2$ hybridized carbons occurs via the pi electron clouds above and/or below the planes of the carbonyl groups.
Figure 6:
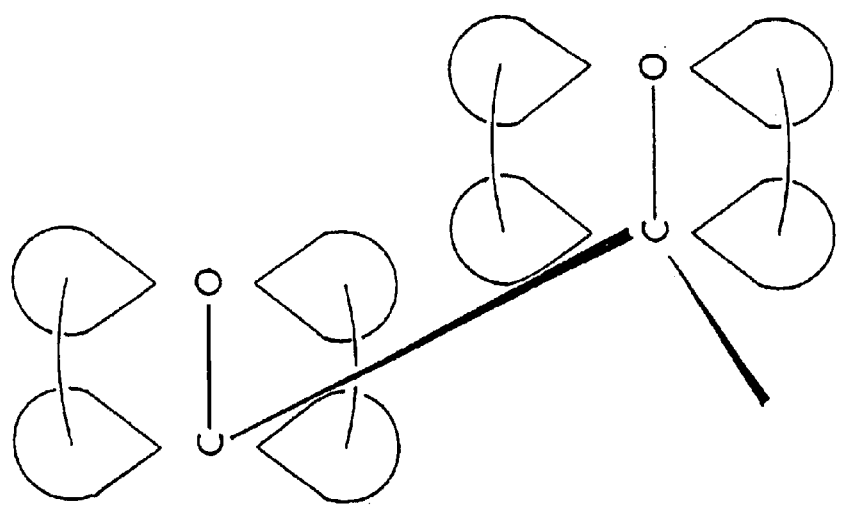

Further regarding the pi electron structure shown in FIG. 6, it is believed that, although the inventors do not intend to be limited by a particular theory, it is this electron structure that makes dicarbonyl groups so reactive, both with native proteins and with the blocker of the instant invention, arginine. Attack on the $sp^2$ hybridized carbons occurs via the pi electron clouds above or below the planes of the carbonyl groups, thusly, both the L and D forms of arginine attack well.

The present invention comprises the use of L-arginine and/or D-arginine to prevent the linking of methylglyoxal, glyoxal, and all dicarbonyl metabolites to protein in human and mammalian tissues and to prevent the cross-linking of these proteins.

The Examples presented herein show that a solution of liquid methylglyoxal reacts with liquid bovine serum albumin to form a gelatin at body temperature in a variety of strongly buffered and pH adjusted systems. The present invention demonstrates the ability of D-arginine to block the cross-linking reaction of methylglyoxal and protein in bovine serum albumin in vitro and maintain the albumin in a liquid state.

Conventional wisdom has it that guanidine and aminoguanidine should block methylglyoxal and glyoxal from cross-linking protein albumin and that glycocyamine and any number of amino acids should work, including, sulfhydryl-containing amino acids. However, the present inventor has tested these compounds and they do not behave as good blockers of or protectant agents against the cross-linking of albumin by methylglyoxal or glyoxal. Remarkably, aminoguanidine is in early human trials as a preventative agent of the formation of advanced glycation end products (AGEs). Among those compounds which the present inventor has tested which do not block the cross-linking reactions are cysteine, cystine, creatine, creatinine, glycocyamine, urea, ornithine, citrulline, cystieamine, aminoguanidine, diaminoguanidine, guanidine and a variety of others, both D and L forms. Glycocyamine, ornithine, citrulline, aminoguanidine, diaminoguanidine, and guanidine are chemically similar to arginine but did not work. It is believed that they did not function as protectants and scavengers of methylglyoxal because they lack the appropriate side groupings. Compounds such as guanidine hydrochloride might also not function as effective scavengers, for example in vivo, because of their tendency to unfold or disrupt protein structure (see, e.g., Smith J. S. and Schotz, J. M.; and Zhang, Y L et al.). Indeed, the only agents which worked consistently were the hydrochloride salts and free base forms of D-arginine and L-arginine.

As described below, the present inventor has reacted methylglyoxal in both buffered and unbuffered systems at pH 6.4 to 11 and found that methylglyoxal binds albumin more effectively at acidic pH levels. In acidic solution one millimole of methylglyoxal is capable of converting 2 cc bovine serum albumin to gelatin at room temperature, but that one millimole of L-arginine or D-arginine can be used to pretreat the bovine serum albumin and will prevent gelatin formation when the methylglyoxal is added.

In acidic and neutral solution pH range 6.4 to 7.4 one millimole of methylglyoxal is capable of converting 2 cc of a liquid 30% solution of bovine serum albumin to gelatin at room temperature, 75, 80, 83, 90 and 98.6 degrees Fahrenheit. When, however, the liquid bovine serum albumin is pretreated with one millimole of either L-arginine or D-arginine prior to the addition of the one millimole of methylglyoxal to the bovine serum albumin, then, the methylglyoxal fails to convert the bovine serum albumin from liquid to gelatin and the albumin remains liquid.

The instant studies have shown that methylglyoxal does not bind bovine serum albumin well at pH 8 to 11, but does produce a solid gelatin at pH 6.4 to 7.4. Both buffered and unbuffered systems were tested.

L-arginine is subject to enzymatic activity and is biologically active in diverse processes, e.g., (1) several isoforms of nitric oxide synthetase produce nitric oxide from L-arginine enzymatically but not D-arginine (Morikawa, E., et.al.); (2) nitric oxide plays an unclear role in septic shock (Wolfe, T. A., et.al.); (3) dietary L-arginine increases levels of interleukin 1 alpha in patients with diabetes mellitus (Hayde, M., et.al.); (4) paradoxically L-arginine and nitric oxide have beneficial effect in protecting against the neurotoxicity produced in the corpus striatum of rats by the 1-methyl4-phenylpyridinium ion (Santiago, M., et.al.); (5) when infused into the rat L-arginine induces the release of glucagon and insulin markedly and slightly increases levels of somatosatin (Takahashi, K., et.al.); (6) L-arginine can aggravate gastric injury produced by ethanol in rats through mechanisms both dependent on and independent of nitric oxide (Ferraz, J. G., et.al.); (7) L-arginine reduces heart collagen accumulation in the diabetic db/db mouse (Khaidar, A., et.al.). There is a plethora of beneficial and harmful effects attributed to L-arginine. It may, nevertheless, have a beneficial effect in diabetes and in the prevention of protein cross-linking.

There are no known enzymatic pathways for D amino acids in the human body. Accordingly, D-arginine is a good candidate for use as a scavenger of methylglyoxal, glyoxal and other glycation products which contain 2 adjacent carbonyl groupings as in the case of deoxyglucosone. Both L-arginine and D-arginine are good candidates for scavenging and blocking single carbonyl groups and dicarbonyl molecules separated by one or more carbons or substituted groups. The reaction between the guanidino group of D-arginine and the dicarbonyl grouping of, e.g., methylglyoxal is a straightforward, pH-dependent, non-enzymatic reaction.

The reaction between methylglyoxal and albumin produced a decrease in pH over time as the reaction progressed. Though the pH of arterial blood and interstitial fluid normally ranges between 7.35 and 7.45 and the generalized systemic pH values compatible with life extend from 6.8 to 7.8 (Wyngaarden, J. B., et.al.), even lower localized pH levels compatible with life have been identified in living brain (Eleff, S. M., et.al.), muscle (Mannion, A. F., et.al.), and blood (Bevington, A., et.al.). At lower pH levels the crosslinking reaction occurs even more rapidly and in this fashion the reaction feeds on itself. In ischemic tissues the local hypoxia produces localized tissue acidosis which is an ideal condition for the reaction between dicarbonyls, e.g., methylglyoxal, and protein-bound or free arginine to progress rapidly. Even at only slightly acidic pH levels serum albumin treated with methylglyoxal becomes visibly syrupy and viscous. This could aggravate local tissue anoxia in living systems, decrease the local tissue pH further, and accelerate protein cross-linking.

As used herein, "subject" can refer to a human patient or a non-human animal in need of treatment.

The present invention comprises primarily the use of arginines (free base forms and hydrochloride salts thereof) and appropriate related chemicals to block cross-linking reactions of toxic dicarbonyls, such as methylglyoxal and glyoxal, with proteins in mammals. However, the medication of the present invention to be administered to a subject could comprise any compound containing an L-arginine or D-arginine structure in which a reactive site is sterically unhindered or can become sterically unhindered in the subject's body (as in the case of a pro-drug). Further, the medication of the present invention to be administered to a subject could comprise any compound containing a structure functionally similar to an L-arginine or D-arginine structure in which a reactive site is sterically unhindered or can become sterically unhindered in the subject's body (as in the case of a pro-drug) such as, but not limited to, custom-designed (engineered) carbohydrates and the like.

The present invention includes the treatment of the human or non-human subject's blood, blood products, and/or plasma (including that derived from recombinant DNA) which is removed to an extracorporeal site such as a renal dialysis apparatus, or other extracorporeal storage or apparatus, and returned to the original host. The present invention includes treatment of donor blood or blood products of human or non-human origin including that derived from recombinant DNA prior to transfer to another human or non-human host, apparatus, or storage site for indeterminate future usage whether ultimately used or not due, for example, to spoilage.

Concentration(s) of arginine hydrochloride, free arginine, or functionally similar compounds could be administered to the extracorporeal blood or blood products or plasma, as filterable wash or unremoved treatment at concentrations of, for example, 0.005 mg/100 ml to 60 mg/100 ml of blood or blood products, but more preferably 4 mg/100 ml to 40 mg/100 ml. In some cases, the arginine or arginine-containing compound is preferably D-arginine or a D-arginine-containing compound, while in other cases, the arginine or arginine-containing compound is preferably L-arginine or a L-arginine-containing compound, while in still other cases, the arginine or arginine-containing compound may preferably include both D-arginine and L-arginine or compounds containing L-arginine and compounds containing D-arginine or a stereoisomeric and/or racemic modification.

Arginine hydrochloride could be administered to the extracorporeal blood or blood products or plasma, as filterable wash or unremoved treatment at concentrations of, for example, 0.001 mg/100 ml to 60 mg/100 ml of blood or blood products or plasma, but more preferably 0.005 mg/100 ml to 50 mg/100 ml of blood or blood products or plasma, and most preferably 0.5 mg/100 ml to 40 mg/100 ml of blood or blood products or plasma. Free arginine, arginine-containing compounds, or functionally similar compounds could be used, alone or in combination, at concentrations such that the amount of available arginine is equal or approximately equal to the amount of available arginine in the ranges in the preceding sentence. It is recognized that smaller treatment quantities could be used for repeated treatments. In some cases, the arginine or arginine-containing compound is preferably D-arginine or a D-arginine-containing compound, while in other cases, the arginine or arginine-containing compound is preferably L-arginine or a L-arginine-containing compound or a stereoisomeric and/or racemic modification.

The free L-arginine or D-arginine, L-arginine hydrochloride or D-arginine hydrochloride, L-arginine-containing compound or D-arginine-containing compound, substituted or modified L-arginine or D-arginine including stereoisomeric modifications and racemic modifications can be administered in extracorporeal blood or blood products or plasma, as filterable wash or unremoved treatment in concentrations as low as $3 \times 10^{-7}$ equivalents per 100 ml and as high as $3.33 \times 10^{-1}$ equivalents per 100 ml depending upon temperature, volume being treated, pH of the host tissue, the presence of particulate matter, the frequency of washings and/or treatments, the desired clinical outcome, patient's tolerance, fragility of the red blood cells, the presence of auto-antibodies, the presence of infectious agents, the presence of antibodies to the infectious agents, the sedimentation rate, the specific gravity of the solution, concentrations of glucose, concentrations of methylglyoxal, concentrations of glyoxal, concentrations of deoxyglucosone, concentrations of malondialdehyde or other carbonyls or dicarbonyls. For these purposes, an "equivalent" of free arginine weighs 174.2 grams.

The extracorporeal treatment could be done in a manner and/or apparatus which is the same as or similar to the manner and/or apparatus disclosed in U.S. Pat. No. 5,626,760 or U.S. Pat. No. 5,567,320, or any of the patents or patent documents cited therein, including U.S. Pat. Nos. 4,056,467; 4,238,340; 4,508,622; 4,668,400; 4,749,619; 4,834,882; 4,923,613; 4,925,534; 4,950,395 5,100,554; 5,145,583; 5,230,702; 5,236,592; 5,399,157; 5,403,497; 5,436,275; and German Patent Document No. 2758679 (July 1979), EP Document No. 0291421 (November 1988), EP Document No. 428927 (November 1989), and EP Document No. 547025 (June 1993), all of which are hereby incorporated by reference.

For a person weighing 70 kg, it is suggested, but not in a limiting sense, that the therapeutically effective daily amount of the medication of the present invention could comprise from about 400 mg to about 1700 mg of free base forms of D-arginine, from 500 mg to 2000 mg of hydrochloride salts of D-arginine, from about 400 mg to about 1700 mg of free base forms of L-arginine, or from 500 mg to 2000 mg of hydrochloride salts of L-arginine. For example, one half of this amount could be administered 2 times per day, 15–30 minutes prior to meals, or one third of this amount could be administered 3 times per day, 15–30 minutes prior to meals. A therapeutically effective daily amount of the medication of the present invention could comprise racemic mixtures of L-arginine and D-arginine, either free base forms, hydrochloride salts, or both. A therapeutically effective daily amount of the medication of the present invention can be administered orally or parenterally (in which case about one fifth of the dose would be used). The medication could be administered chronically or in emergency situations. Implants or time-release forms could be used as well.

Another method of treating a subject under the present invention could be to administer L-citrulline or another precursor of L-arginine in the urea cycle to produce the L-arginine in the subject's body. Yet another method of treating a subject could be to administer a compound containing a structure functionally similar to L-citrulline or another precursor of L-arginine in the urea cycle to produce the L-arginine in the subject's body.

In order to illustrate the present invention, the following examples are provided. It is to be understood that the following examples are to be taken merely in an illustrative sense and are not intended to limit the invention in any manner.

EXAMPLE 1

As described in TABLE #4, 2 cc of 30% bovine serum albumin (BSA) was added by glass pipette (Kimax 1/100) to each of three glass 7 ml. test tubes numbered 1, 2, and 3. 0.4 ml. of 6 molar HEPES buffer was added to tube #1 by glass pipette. 0.5 ml. of 6 molar HEPES buffer was added to test tube #2. 0.3 ml. of 6 molar HEPES buffer was added to tube #3. (HEPES salt, HEPES acid, and bovine serum albumin was obtained from Sigma.) Tubes 1, 2 and 3 were placed in a warm water bath at 98.6 degrees Fahrenheit with PTFE-coated microflea magnetic stirrer bars on a magnetic stirrer at 217 RPM for 5 minutes.

Next, 0.18 ml. of 40% methylglyoxal (pH not adjusted) was added to test tube #1. 0.10 ml. of 40% methylglyoxal (buffered with 0.3 cc of 6 molar HEPES to pH 7.44 at 98.6 degrees Fahrenheit) was added to test tube #2. 0.20 ml. of 40% methylglyoxal (buffered with 0.3 cc of 6 molar HEPES to pH 7.36 at 98.6 degrees Fahrenheit) was added to test tube #3.

At 98.6 degrees Fahrenheit and a stir rate of 217 RPMs all formed a gel.

EXAMPLE 2

As described in TABLE #5, 2 cc of 30% bovine serum albumin was added by glass pipette to each of 6 glass 7 ml. test tubes numbered 1 through 6. 1 millimole of L-arginine hydrochloride in 0.5 ml. of 6 molar HEPES buffer was added to tube #1. 1 millimole of L-arginine hydrochloride in 0.4 ml. of 6 molar HEPES buffer was added to tube #2. 1 millimole D-arginine hydrochloride in 0.5 ml. of 6 molar HEPES buffer was added to tube #3. 1 millimole D-arginine hydrochloride in 0.4 ml. of 6 molar HEPES buffer was added to tube #4. 0.5 ml. of 6 molar HEPES buffer was added to tube #5. 1 millimole of glycocyamine in 0.5 ml. of 6 molar HEPES buffer was added to tube #6.

All tubes were stirred with microflea magnetic bars at 217 RPM at 98.6 degrees Fahrenheit for 5 minutes and the pH measured with a Hanna pH meter using a single junction Hanna glass electrode.

One millimole (0.18 ml. of 40% solution) of methylglyoxal was added to each sample by glass pipette at a constant temperature of 98.6 degrees Fahrenheit and a stir rate of 217 RPM. The pH was measured periodically and observations were made and recorded. At three hours the heating unit was reduced to room temperature, 75 degrees Fahrenheit, to prevent drying and the reaction allowed to proceed.

Importantly, the results in Table 2 show that both L- and D-arginine effectively block methylglyoxal cross-linking of bovine serum albumin.

EXAMPLE 3

As described in TABLE #6, 2 ml. bovine serum albumin 30% solution was added to each of eight 7 ml. glass test tubes. One millimole of guanidine was added to tube #1; no protectant was added to tubes #2, #3, and #4. Into test tube #5 was added 1 millimole of D-arginine hydrochloride producing an initial pH of 5.91 which was adjusted to pH 7.46 by micro-drop titration with one molar NaOH and 2N HCl using a 25 gauge needle on a glass syringe. Into test tube #6 was added 1 millimole of L-arginine hydrochloride, the pH was adjusted to 7.40 by micro-drop titration. Into test tube #7 was added 1 millimole of L-arginine hydrochloride, not pH adjusted. Into test tube #8 was added 1 millimole of D-arginine hydrochloride, not pH adjusted. To each of the tubes sample numbers 1 through 8 pH-adjusted methylglyoxal was added as described in column C. Again the pH was recorded for each sample and observations listed in the table. Sample numbers 1, 2, 3 and 4 formed a distinguishable gel. Sample numbers 5, 6, 7 and 8 remained liquid. After 3 hours the heating unit was turned off reducing the temperature to room temperature, 75 degrees Fahrenheit, to prevent the drying out of the sample and the reaction was allowed to proceed overnight. Sample #7 became slightly viscous overnight.

As in Table 5, the results presented in Table 6 confirm that both L- and D-arginine are effective blockers of toxic dicarbonyl induced cross-linking of proteins and adduct formation.

EXAMPLE 4

As described in Table 7,2 ml. of a 30% aqueous solution (0.85% NaCl) of bovine serum albumin was added to each glass test tube and placed in a 98.6 F. warm water bath with a microflea magnetic stirrer bar in each tube. The magnetic stirrer was set to 217 rpm. The pH was checked at five minutes. The B.S.A. was buffered to the desired pH with 6 molar HEPES by slow addition of the buffer to the albumin at 98.6 F. and 217 rpm until the pH was stable.

In separate glass test tubes 0.18 ml. of a 40% methylglyoxal aqueous solution, 1 millimole, was added and buffered to the desired pH with 6 molar HEPES buffer at 98.6 F. Total volume was adjusted with deionized water.

The glass electrode of the pH meter (Hanna) was placed in the test tube with the buffered albumin and the buffered methylglyoxal was added slowly with a 25 gauge needle on a glass syringe. The pH was constantly monitored as were the color and fluid characteristics of the mixture. The mixing speed was constant at 217 rpm at a temperature of 98.6 F. The tubes were tilted periodically to determine fluidity, viscosity, color and gel formation. The end-point was recorded when a visible non-flowing gel formed in the tube and could not be caused to flow when the tube was inverted at 40 degrees below the horizontal for two minutes. At this point the gelatin was adherent to the glass pH electrode. Often the gelatin could be removed as a solid mass. At lower pH levels the gel had the consistency of firm rubber and at more neutral pH the consistency was that of soft gelatin.

The albumin samples which were pretreated with 1 millimole of the D-arginine Hydrochloride or 1 millimole of L-arginine Hydrochloride did not gel at any time and remained liquid.

EXAMPLE 5

Example 5 shows the in vivo use of both D- and L-arginine in the prevention or reduction of signs of diabetes in an animal model.

50 young adult male New Zealand White rabbits are divided into five groups of ten and fed standard veterinary rabbit pellet food. All rabbits are made diabetic by streptozotocin injection (65 mg/kg administered i.v. per the technique of R. Burcelin, (1993) J. Biochemistry 291:109, which is hereby incorporated by reference). In all groups except Group 1, the arginine protectant is administered concurrently in the diet or prior to the challenge with radiolabeled methylglyoxal per i.v.

Group 1: Using a 25 gauge needle and i.v. apparatus, 1 millimole of radiolabeled methylglyoxal (e.g., tritiated or carbon 14 labeled) (or an appropriate dose, for example, but not limited to ranging from 1 nmole to a sublethal dose, such as the LD50 of methylglyoxal which is reported to be 252 mg/kg in rats; Ceskoslovenska Farmacie, (1966) 15:300, which is hereby incorporated by reference) in 10 cc of normal saline is administered per day by ear vein over a 2-hour period. This is repeated daily for 30, 60, 90, 120 or some other appropriate number of days.

Group 2: The rabbits of group 2 are fed a diet supplemented with oral D-arginine HCL 30 mg/kg/day (or an appropriate dose which can range from, for example, but not limited to, 1 mg/kg/day to 100 mg/kg/day). As described above for Group 1, the rabbits in Group 2 are administered an identical regime of radiolabeled methylglyoxal as the control group, Group 1 (for example, 1 millimole of tritiated methylglyoxal in 10 cc normal saline is administered by ear vein over a period of 2 hours per day for, for example, 30 days).

Group 3: The rabbits of group 3 are fed a diet supplemented with oral L-arginine HCL 30 mg/kg/day (or an appropriate dose which can range from, for example, but not limited to, 1 mg/kg/day to 100 mg/kg/day). As described above for Group 1, the rabbits in Group 3 are administered an identical regime of radiolabeled methylglyoxal as the control group.

Group 4: The rabbits of group 4 receive L-arginine HCL by ear vein in 10 cc normal saline at a dose of 10 mg/kg/day (or an appropriate dose which can range from, for example, but not limited to, 1 mg/kg/day to 100 mg/kg/day) for the duration of the experiment. As described above for Group 1, the rabbits in Group 4 are also administered an identical regime of radiolabeled methylglyoxal as the control group. The arginine protectant is administered i.v. for a 2-hour period immediately preceding administration of the methylglyoxal.

Group 5: The rabbits of group 5 receive D-arginine HCL by ear vein in 10 cc normal saline at a dose of 10 mg/kg/day (or an appropriate dose which can range from, for example, but not limited to, 1 mg/kg/day to 100 mg/kg/day) for the duration of the experiment. As described above for Group 1, the rabbits in Group 5 are also administered an identical regime of radiolabeled methylglyoxal as the control group. The arginine protectant is administered i.v. for a 2-hour period immediately preceding administration of the methylglyoxal.

At the end of the experiment, all animals are sacrificed and their kidneys removed, sectioned and examined for gross and microscopic changes, as well as for accumulation of the radiolabel, with special attention to the glomerular basement membrane.

This experiment shows that in control rabbits made diabetic with streptozotocin, both gross and microscopic changes in the kidney are observed and also the accumulation of radiolabeled methylglyoxal in the kidney is observed. It is believed that the radiolabeled kidney accumulation is related to toxic cross-linking of the radiolabeled toxic dicarbonyl-containing methylglyoxal that was administered.

The experimental groups, on the other hand, show that the administration of the dicarbonyl blocker arginine, both D- and L-, and both i.v. and by mouth, effectively blocks the detrimental effects of methylglyoxal in vivo. This is shown by the reduced or absent gross and microscopic changes in the kidney of the treated animals as compared to the control, and by the reduced or absent accumulation of radiolabeled methylglyoxal in the kidneys of the arginine-treated animals as compared with the control.

This experiment shows that both D- and L-arginine can serve as a protectant against methylglyoxal-induced tissue change when administered prophylactically.

EXAMPLE 6

Example 6 shows the in vivo use of both D- and L-arginine in the prevention or reduction of symptoms of diabetes in an animal model.

50 young adult male New Zealand White rabbits are divided into five groups of ten and fed standard veterinary rabbit pellet food. All rabbits are made diabetic by streptozotocin injection (65 mg/kg administered i.v. per the technique of R. Burcelin, (1993) J. Biochemistry 291:109, which is hereby incorporated by reference). In all groups except Group 1, the arginine protectant is administered concurrently in the diet or prior to the challenge with radiolabeled glucose per i.v.

Group 1: Using a 25 gauge needle and i.v. apparatus, a solution of radiolabeled glucose, for example, but not limited to a 10% solution of tritiated or carbon 14 labeled glucose, is administered by ear vein over, for example, a 2-hour period per day. This is repeated daily for 30, 60, 90, 120 or some other appropriate number of days.

Group 2: The rabbits of group 2 are fed a diet supplemented with oral D-arginine HCL 30 mg/kg/day (or an appropriate dose which can range from, for example, but not limited to, 1 mg/kg/day to 100 mg/kg/day). As described above for Group 1, the rabbits in Group 2 are administered an identical regime of radiolabeled glucose as the control group, Group 1 (for example, a 10% solution of tritiated glucose administered by ear vein over a period of 2 hours per day for, for example, 30 days).

Group 3: The rabbits of group 3 are fed a diet supplemented with oral L-arginine HCL 30 mg/kg/day (or an appropriate dose which can range from, for example, but not limited to, 1 mg/kg/day to 100 mg/kg/day). As described above for Group 1, the rabbits in Group 3 are administered an identical regime of radiolabeled glucose as the control group.

Group 4: The rabbits of group 4 receive L-arginine HCL by ear vein in 10 cc normal saline at a dose of 10 mg/kg/day (or an appropriate dose which can range from, for example, but not limited to, 1 mg/kg/day to 100 mg/kg/day) for the duration of the experiment. As described above for Group 1, the rabbits in Group 4 are also administered an identical regime of radiolabeled glucose as the control group. The arginine protectant is administered i.v. for a 2-hour period immediately preceding administration of the methylglyoxal.

Group 5: The rabbits of group 5 receive D-arginine HCL by ear vein in 10 cc normal saline at a dose of 10 mg/kg/day (or an appropriate dose which can range from, for example, but not limited to, 1 mg/kg/day to 100 mg/kg/day) for the duration of the experiment. As described above for Group 1, the rabbits in Group 5 are also administered an identical regime of radiolabeled glucose as the control group. The arginine protectant is administered i.v. for a 2-hour period immediately preceding administration of the methylglyoxal.

At the end of the experiment, all animals are sacrificed and their kidneys removed, sectioned and examined for gross and microscopic changes, as well as for accumulation of the radiolabel, with special attention to the glomerular basement membrane.

This experiment shows that in control rabbits made diabetic with streptozotocin, both gross and microscopic changes in the kidney are observed and also the accumulation of radiolabeled glucose metabolites in the kidney is observed. It is believed that the radiolabeled kidney accumulation is related to toxic cross-linking of radiolabeled toxic dicarbonyl-containing glucose metabolites such as methylglyoxal.

The experimental groups, on the other hand, show that the administration of the dicarbonyl blocker arginine, both D- and L-, and both i.v. and by mouth, effectively blocks the detrimental effects of diabetes, at least on the kidney, in vivo. This is shown by the reduced or absent gross and microspopic changes in the kidney of the treated animals as compared to the control, and by the reduced or absent accumulation of radiolabeled glucose metabolites in the kidneys of the arginine treated animals as compared with the control.

This experiment shows that both D- and L-arginine can serve as a protectant against diabetes-related kidney changes when administered prophylactically.

EXAMPLE 7

Example 7 is identical to Example 5 except that the animals are not made diabetic by streptozotocin. Also, the amount of radiolabeled high as a sub-lethal dose, the LD50 for methylglyoxal being reported as being 252 mg/kg (Ceskoslovenska Farmacie, (1966) Vol. 15, page 300).

This example shows that arginine blocks changes caused by methylglyoxal even in a non-diabetic animal model.

EXAMPLE 8

Example 8 shows the in vivo use of both D- and L-arginine in the reduction of the level of toxic methylglyoxal in an animal.

50 young adult male New Zealand White rabbits are divided into five groups of ten and fed standard veterinary rabbit pellet food. Using a 25 gauge needle and i.v. apparatus, 1 millimole of methylglyoxal (or an appropriate dose, for example, but not limited to ranging from 1 nmole to a sub-lethal dose) in 10 cc of normal saline is administered per day by ear vein over a 2-hour period to all animals. This is repeated daily for 30, 60, 90, 120 or some other appropriate number of days. In all groups except Group 1, the arginine protectant is administered concurrently in the diet or prior to the challenge with radiolabeled methylglyoxal per i.v.

Group 1: The rabbits of control group 1 are not administered any arginine but are administered methylglyoxal in a manner identical to the experimental groups (e.g., 1 millimole of methylglyoxal per day for 30 days).

Group 2: The rabbits of group 2 are fed a diet supplemented with oral D-arginine HCL 30 mg/kg/day (or an appropriate dose which can range from, for example, but not limited to, 1 mg/kg/day to 100 mg/kg/day). As described above for Group 1, the rabbits in Group 2 are administered an identical regime of methylglyoxal as the control group, Group 1.

Group 3: The rabbits of group 3 are fed a diet supplemented with oral L-arginine HCL 30 mg/kg/day (or an appropriate dose which can range from, for example, but not limited to, 1 mg/kg/day to 100 mg/kg/day). As described above for Group 1, the rabbits in Group 3 are administered an identical regime of methylglyoxal as the control group.

Group 4: The rabbits of group 4 receive L-arginine HCL by ear vein in 10 cc normal saline at a dose of 10 mg/kg/day (or an appropriate dose which can range from, for example, but not limited to, 1 mg/kg/day to 100 mg/kg/day) for the duration of the experiment. As described above for Group 1, the rabbits in Group 4 are also administered an identical regime of methylglyoxal as the control group. The arginine protectant is administered i.v. for a 2-hour period immediately preceding administration of the methylglyoxal.

Group 5: The rabbits of group 5 receive D-arginine HCL by ear vein in 10 cc normal saline at a dose of 10 mg/kg/day (or an appropriate dose which can range from, for example, but not limited to, 1 mg/kg/day to 100 mg/kg/day) for the duration of the experiment. As described above for Group 1, the rabbits in Group 5 are also administered an identical regime of methylglyoxal as the control group. The arginine protectant is administered i.v. for a 2-hour period immediately preceding administration of the methylglyoxal.

At appropriate intervals during the experiment, for example, but not limited to every 5 days, blood samples are withdrawn from the animals and the level of methylglyoxal in the blood of each animal is assayed as described (Haik et al. (1994) Methylglyoxal concentration and glyoxalase activities in the human lens, Exp. Eye Res. 59:497–500, which is hereby incorporated by reference).

This experiment shows that the administration of arginine in vivo reduces the level of toxic, cross-linking methylglyoxal in a living system.

The Tables found in Appendix 2 after the claims illustrate the invention, and its various embodiments, as described and referenced above.

EXAMPLE 9

Example 9 shows the in vivo use of L-arginine in the reduction of the level of toxic methylglyoxal a human.

L-arginine hydrochloride given to a 120kg, 75 year old insulin dependent diabetic male in a dose of 700 mg of L-arginine hydrochloride twice a day (1,400 mg per day) for painful feet secondary to vasculopathy and/or neuropathy, resulted in a marked reduction in pain in both the feet and hands after treatment with arginine within 6 weeks.
PDGF The following references listed in Appendix I are especially useful to understand how the present invention prevents damage to or inactivation of Platelet Derived Growth Factor (PDGF), PDGF-AA, PDGF-BB, PDGF-AB, PDGF-A, PDGF-B, by preventing linkage to cysteine, cysteine bonds, lysine, and/or arginine moieties in these growth factors by administering to a subject orally, parenterally, and/or extracorporeally L-arginine or D-arginine, modified or substituted arginine, or an amino acid or a polypeptide or a carbohydrate modified to serve as an arginine: Lindahl et al., Mesecar et al., Sigma Chemical Company, Ross et al., Betsholtz et al., Giese et al., and Sauer et al. In FIG. 6 (at page 1318) of the Giese et al. reference there is a good depiction of cysteine residues in PDGF molecules.

Dicarbonyls such as methylglyoxal, malondialdehyde, deoxyglucosone, and glyoxal can react with the cysteine, lysine, and arginine moieties of structural and functional proteins. Functional proteins such as platelet derived growth factor-B (PDGF-B) function, in part at least, on a "lock and key" mechanism. The tertiary structure, indeed the functional structure, of PDGF-B is dependent greatly upon the intra- and inter-chain disulfide bonds produced by 8 cysteine residues numbered 127, 154, 160, 163, 164, 171, 208, 210. Especially of importance are residues 127, 160, 171, 208.

It is the theory of the present inventor that inasmuch as methylglyoxal preferentially attacks arginine, cysteine and lysine that the cysteine-based intra- and inter-chain bonds of PDGF-B (and the PDGF family of growth factors) are attacked and rendered nonfunctional by methylglyoxal and/or other dicarbonyls. Methylglyoxal is present in excessive amounts in diabetic blood. Methylglyoxal and other dicarbonyls, such as a glyoxal, malondialdehyde, and deoxyglucosone to name a few, would potentially have the same or similar detrimental effect(s) upon the tertiary structure (as well as secondary structures, quaternary structures, charge distribution, and protonation) of PDGF and other functional and structural proteins.

Destruction of the normal configuration, especially the disulfide bonding, of e.g. PDGF-B, renders it inactive. Methylglyoxal and other dicarbonyls can attack the cysteines which originate the disulfide bonds. L-arginine, D-arginine, racemic mixtures, derivatives of L and/or D arginine, and structural analogues and chemical mimics can block and/or scavenge the dicarbonyls(s) attacking the cysteines involved in disulfide bonding.

Mice which are genetically deficient in PDGF-B exhibit loss of microvascular capillary pericytes, capillary microaneurysms, and the endothelial cells of developing capillaries seem unable to attract PDGF-Rβ-positive pericyte progenitor cells. In diabetic humans, one also observes loss of microvascular capillary pericytes and development of capillary microaneurysms. Lacking the normal pericyte structure, microaneurysms can form. Lindahl et al. have also noted a deficiency of myofibroblasts and a mesangial cell general deficiency in mice which are genetically deficient in PDGF-B.

In the inventor's theory the cause of PGDF deficiency is the attack on and inactivation of disulfide bonding by methylglyoxal and similar listed dicarbonyls which can be prevented by use of L-arginine, D-arginine, racemic mixtures of L and D arginine, substituted arginine, arginine analogues and chemical mimics, prodrugs of arginine, precursors of arginine in the Urea Cycle, and compounds containing the essential arginine nucleus in free base form, salt form, or attached to a carrier protein, including genetically engineered and mono or polyclonally produced forms.

The present inventor hypothesizes that a similar process is at work in the activity of substances such as methylglyoxal and malondialdehyde and other dicarbonyls in the microvasculature in diabetic eye disease, coronary artery disease, microvasculature disease of the eyes, kidneys and extremities and in diabetic and non-diabetic microvascular disease of the heart and coronaries.

It is well known to physicians that diabetics exhibit increased blood viscosity. A "sludging" of the blood is noticeable on fluorescein angiography of the retinal capillaries of diabetics. Increased viscosity of the blood and serum albumin, as well as other blood products, may well contribute to hypoxic disease and promote thrombosis of, e.g., retinal capillaries and the peripheral vasculature of, especially, the toes, feet and legs of diabetics. Diabetes is the most common cause of vascular occlusion leading to amputation of the toes, feet, and legs.

Increased viscosity of plasma, serum, and albumin is especially noticeable in type 1 (insulin dependent) diabetics and they develop vascular complications earlier than type 2 (non-insulin dependent) diabetics (ref: Memeh). With time both type 1 and type 2 diabetics develop vascular abnormalities. As the inventor has shown (Table 7) methylglyoxal causes an increase in serum viscosity over time which can lead to gel formation with a drop in pH. The inventor has shown (Tables 5 and 6) that L and D arginine block this effect. The substantial buffering power of blood proteins and/or a lesser concentration of methylglyoxal would easily produce increased viscosity of serum albumin without visible gel formation. This would contribute to vascular sludging and hypoxia without a serum albumin gel "thrombus". Gel formation, at higher concentrations of methylglyoxal and proper pH could, nevertheless, occlude appropriately sized vessels. Memeh, C. U.

As used herein, "relative viscosity" can be measured as in the Memeh reference, but is not limited to that technique.

Recently, the benefit of administering C-peptide to diabetics has been recognized in the literature. (Ido et al. and Steiner et al.).

In accordance with the present invention, to effect the benefits discussed herein, a subject can be administered L-arginine (L-arginine HCL or L-arginine free base) by mouth in divided doses for a total of about 13 grams per 70 kilograms of body weight per day (about 186 mg/kg per day) or is administered an equivalent oral dose per day of D-arginine, modified arginine, substituted arginine, or protein or carbohydrate complex which serves as an arginine, or arginine mimic.

The dosage will depend in part upon the degree of disease state and diabetic control. The following daily oral dosages (preferably divided into two or three administrations per day) are believed to be useful for a person having 70 kg of body weight: for a person with good diabetic control 100 mg–6000 mg; fair diabetic control 6000 mg–13,000 mg; and poor diabetic control 13,000 mg or more. These recommended dosages are of L-arginine (L-arginine HCL or L-arginine free base) by mouth in divided doses or an equivalent oral dose per day of D-arginine, modified arginine, substituted arginine, or protein or carbohydrate complex which serves as an arginine, or arginine mimic.

The foregoing embodiments are presented by way of example only; the scope of the present invention is to be limited only by the following claims.

REFERENCES (All of Which are Incorporated Herein by Reference)

Araki, Norei, et al., Immunochemical Evidence for the presence of advanced glycation end products in human lens proteins and its positive correlation with aging. Journal of Biological Chemistry. 267(15): 10211–10214, May 1992.

Betsholtz, C., et al., (1986). cDNA sequence of individual cysteine residues in the structure and function of the v-sis gene product. Nature 320:695–699.

Bevington, A., et al., Metabolic acidosis is a potent stimulus for cellular inorganic phosphate generation in uraemia, Clinical Science. 88(4):405–12, 1995 April Eleff, S. M., et.al., Acidemia and brain pH during prolonged cardiopulmonary resuscitation in dogs. Stroke. 26(6): 1028–34, 1995 June.

Ferraz, J. G., Tigley, A., Wallace, J. L. (1994) Paradoxical effects of L-arginine on gastric mucosal integrity. European Journal of Pharmacology. 260(1): 107–11.

Geise et al., (1987), The role of individual cysteine residues in the structure and function of the v-sis gene product. Nature. 236: 1315–1318.

Haik Jr., George M., Lo, T. W. C., and Thomalley, P. J. (1994) Methylglyoxal Concentration and Glyoxalase Activities in the Human Lens. Exp. Eye Res. 59.497–500.

Haik Jr., George M., et al., Diabetic Retinopathy: A leading cause of new blindness, Southern Medical Journal. 82(5): 575–579, May 1989.

Hayde, M., Vierhapper, H., Lubec, B., Popow, C., Weninger, M., Xi, Z., Lubec, G. Low-dose dietary L-arginine increases plasma interleukin 1 alpha but not interleukin 1 beta in patients with diabetes mellitus. Cytokine, 6(1): 79–82, 1994 January.

Ido, Y., Vindigni, A., Chang, K., Stramm, L., Chance, R., Heath, W. F., DiMarchi, R. D., Di Cera, E, and Williamson, J. R., "Prevention of vascular and neural dysfunction in diabetic rats by C-peptide", Science, 277:563–566 (July 25, 1997), and Khaidar, A., Marx, M., Lubec, B., Lubec, G. (1994) L-arginine reduces heart collagen accumulation in the diabetic db/db mouse. Circulation. 90(1):479–83.

Lindahl, P., Johansson, B., Leveen, P., Betsholtz, C. (1997), Pericyte Loss and Microaneurysm Formation in PDGF-B-Deficient Mice. Science. 277:242–245.

Mannion, A. F., Skeletal muscle buffer value, fibre type distribution and high intensity exercise performance in man. Experimental Physiology. 80(1):89–101, 1995 January.

Memeh, C. U., "Differences between plasma viscosity and proteins of types 1 and 2 diabetics Africans in early phase of diabetes.", Hormone and Metabolic Research, 25(1): 21–3 (1993).

Mesecar, A., Stoddard, B., Koshland, D., (1997) Orbital Steering in the Catalytic Power of Enzymes: Small structural changes with large catalytic consequences. Science 277:202–206.

Morikawa, E., Huang, Z., Moskowitz, M. A., (1992) L-arginine decreases infarct size caused by middle cerebral arterial occlusion in SHR. American Journal of Physiology. 263(5 pt 2):H1632–5.

Ross, R., Glomset, J., Kariya, B., Harker, L. (1974). A Platelet-Dependent Serum Factor that Stimulates the Proliferation of Arterial Smooth Muscle Cells in vitro. Proc. Nat. Acad. Sci. USA. 71(4):1207–1210.

Santiago, M., Machado, A., Cano, J. (1994) Effect of L-arginine/nitric oxide pathway on MPP(+)-induced cell injury in the striatum of rats. British Journal of Pharmacology. 111(3):837–42.

Sauer, M. et al., (1988). Identification of nonessential disulfide bonds and altered conformations in the v-sis protein, a homolog of the B chain of the platelet-derived growth factor. Molecular and Cellular Biology. 8(3): 1011–1018.

Sigma Chemical Company, (02/1994). Product No. P-4306—Platelet-Derived Growth Factor-BB (2 pp.)

Smith J. S. and Schotz, J M. (1996) Guanidine hydrochloride unfolding of peptide helices: separation of denaturant and salt effects. Biochemistry 35:7292–7.

Steiner, D. and Rubenstein, A., "Proinsulin C-peptide—Biological Activity?", Science, 277:531–532 (July 25, 1997).

Takahashi, K., Yamatani, K., Hara, M., Sasaki, H., (1 994) Gliclazide directly suppresses arginine-induced glucagon secretion. Diabetes Research and Clinical Practice. 24(3): 143–51.

Wolfe, T. A., Dasta, J. F., (1995) Use of nitric oxide synthase inhibitors as a novel treatment for septic shock. (Review). Annals of Pharmacotherapy. 29(1):3646.

Wyngaarden, J. B., and Smith, L. H.; Cecil, Textbook of Medicine, 16th Edition, 1982, pg. 486.

Zhang, Y. L. (1996) Sequential unfolding of adeylate kinase during denaturation by guanidine hydrochloride. Biochemica et Biophysica Acta. 1295:239–44.

TABLE 1

[Chemical structures: various aldehydes, ketones, and ortho-quinone]

TABLE 2

[Structure: guanidino compound with F substitution on NH position]

Substitution with a fluorine atom as shown decreases electron density at the neighboring NH group decreasing its activity as well as slightly decreasing the activity of the entire guanidino group. This is also true for substitutions in this position with $NO_2$, CN, I, and Cl.

[Structure: guanidino compound with $CH_3$ substitution on NH position]

Substitution of a methyl at the position shown would cause an increase in electron density at the neighboring NH group increasing its activity as well as slightly increasing the activity of the entire guanidino group. This is also true for substitution with any alkyl or aryl group.

[Structure: guanidino compound with F at alpha carbon]

Substitution of a fluorine atom for a hydrogen atom as shown would cause the amino attached to the alpha carbon to become less reactive and the carboxylate group to have a reduced pKa. This is also true for $NO_2$, CN, I, Br, and Cl substitution at this position.

[Structure: guanidino compound with $CH_3$ at alpha carbon]

Substitution of a methyl for a hydrogen at the alpha carbon position as shown increases the electron density at the alpha amino group as well as decreasing the activity of the carboxylate group. This is also true for substitution of any alkyl or aryl group in this position.

TABLE 2-continued

[Structure: guanidino compound with methyl ester]

Substitution of a methyl in the position shown decreases solubility of the molecule in aqueous solutions by making the group more hydrophobic.

[Structure: guanidino compound with $NH_2CH_3$ group]

Substitution with a methyl for a hydrogen at the alpha amino group as shown increases the reactivity of the alpha amino nitrogen while making that nitrogen more sterically hindered toward attack. This is also true for substitution at this position of any alkyl or aryl group. The steric effects will increase as the size of the group attached increases to a maximum of $C(CH_3)_3$. The three modifications shown below will lead to an increase in electron density and reactivity at the imino nitrogen.

[Structure: 5-membered cyclic guanidine]

[Structure: 5-membered cyclic guanidine variant]

[Structure: 6-membered cyclic guanidine with S]

[Structure: bridged cyclic guanidine]

Bridging of the imino nitrogen of the guanidine moiety with a methylene group at the delta carbon as shown would form a rigid ring system while increasing the electron density and the reactivity at this nitrogen.

[Structure: cyclic guanidine with sulfone]

Addition of the sulfone group in the ring at the position shown should slightly increase water solubility and possibly increase membrane permeability.

TABLE 2-continued

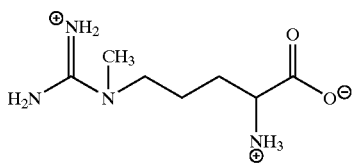

Substitution of a methyl for a hydrogen at the position shown would increase electron density at the guanidino end of the molecule favoring reactivity at that end.

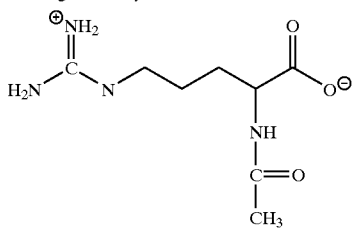

Substitution of an amido group for the amino group, as shown, would produce a less polar zwitterion.

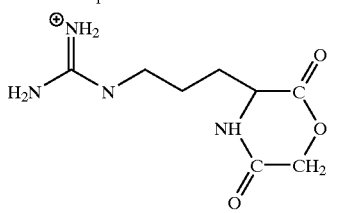

Hydrophilic End         Hydrophobic End

The above arrangement favors ocular (corneal) permeability due to its biphasic structure. This structure may aid penetration of other biological tissues.

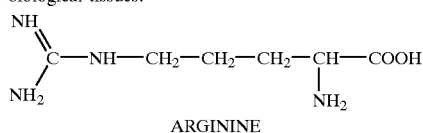

ARGININE

Arginine analogues can be produced by:
1. Modifying the length of the central chain of methylene groups designated by $(CH_2)n$ such that n = 0 or any integer in the following structure:

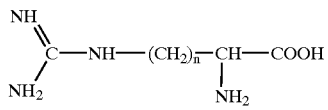

2. Substitution into L or D Arginine (free base or salt) or a sterically similar or homologous compound (organic or inorganic) any straight, branched, and/or any combination of cyclic, substituted or unsubstituted chemical group (5) not to exclude amino acid(s) and protein chains. Some possible substitutions include:

(1)
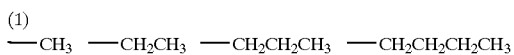

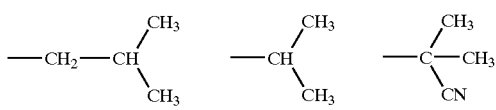

TABLE 2-continued

2)
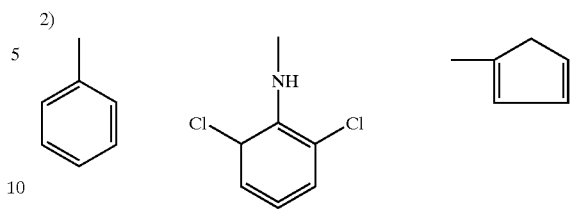

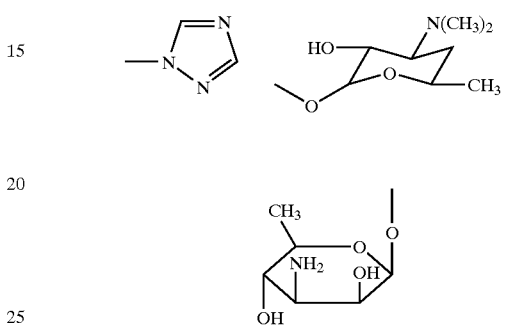

3. Any combination of polypeptide chains consisting at least in part of L-Arginine and/or D-Arginine in whole, part or modified. Including those chains or units substituted with non-amino acid moieties, those attached to monoclonal or polyclonal antibodies, immune globulins, or synthetic products or natural products.

Examples include:      Arg-Lys . . . Phenylamide
                                    Arg-Arg
                                    Arg-Lys-Arg
    Amino acid sequence     $(a.a)_1$-$(a.a)_2$-Arg . . . $(a.a)_x$
                                    Arg-$(a.a)_x$ . . . $(a.a)_y$
                                    $(a.a)_x$ . . . Arg . . . $(a.a)_z$ 4. Substitution with or of any of the following groups in any position:

—OH      hydroxyl

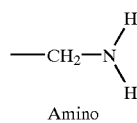

Amino

—C═O      carbonyl

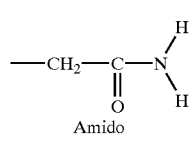

Amido

—COOH      carboxyl

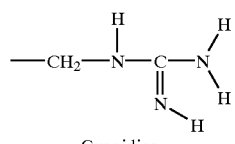

Guanidino

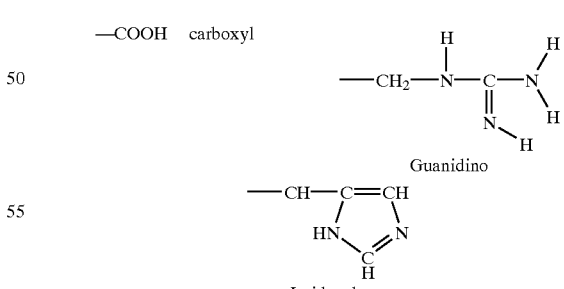

Imidazole

—SH      Sulfhydryl
—S—S      Disulfide

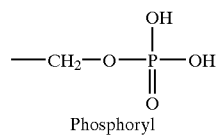

Phosphoryl

TABLE 2-continued

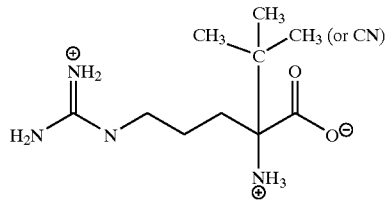

Substitutions as shown above and below of $C_4H_9$ or $C_4H_6N$, the latter of which increases water solubility, would sterically hinder reactions at the carboxylate end of the molecule and favor reactivity at the guanidino end.

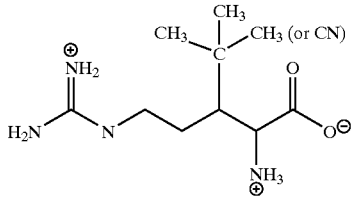

TABLE 2-continued

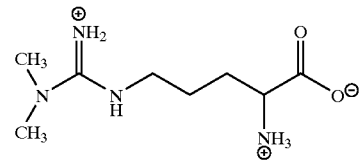

Dimethyl substitution of the single-bonded terminal nitrogen of the guanidino group would cause the guanidino group to become a stronger base and become more reactive due to increased electron density.

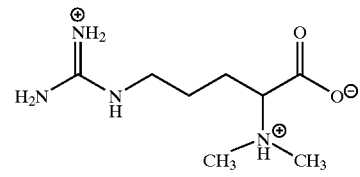

Substitution of the hydrogens on the alpha amino group with $CH_3$ groups would cause the nitrogen of the alpha amino group to produce a strong base.

TABLE 3

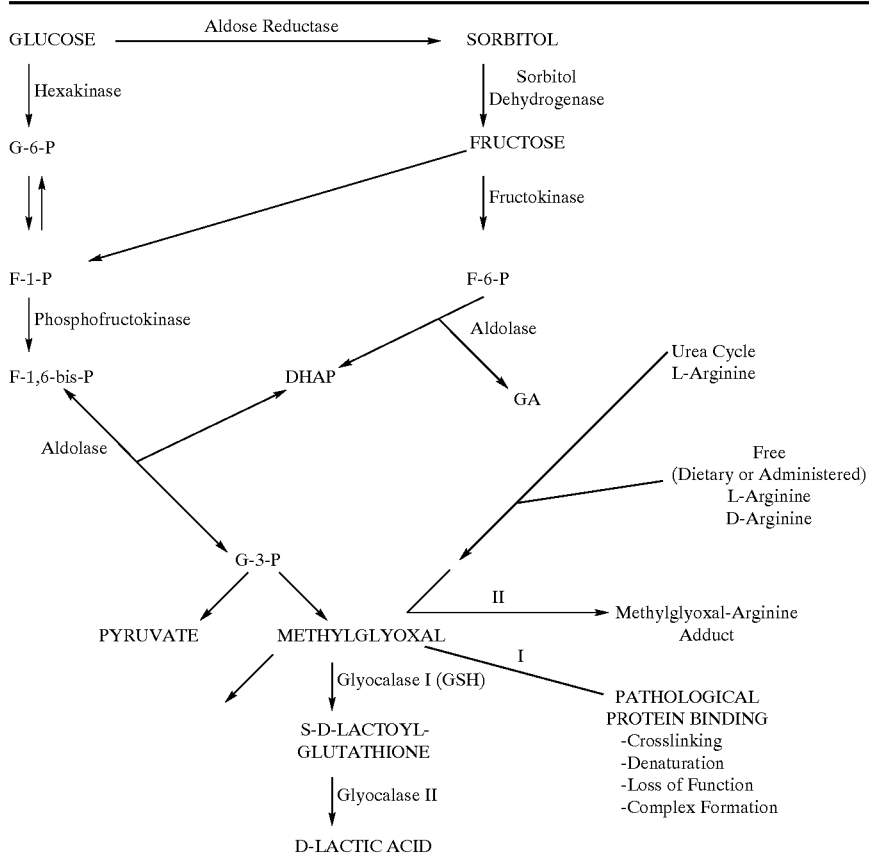

TABLE 4

| | A | | | | | A + B + C REACTION at 98.6° F. | |
|---|---|---|---|---|---|---|---|
| | Bovine Serum Albumin | Buffered B | | pH of A + B | C | | |
| Sample Number | 30% | pH Adjustment | Protectant | Mixture | Reactant | Observation | FINAL FORM |
| 1 | 2 ml | 6 m HEPES 0.4 cc | None | 7.40 at 98.6° F. | 1 millimole of methylglyoxal; 0.18 ml of 40% methylglyoxal | <5 minutes after mixing buffered BSA with reactant a firm yellow gelatin formed; last recorded pH 6.58 at 98.6° F. | FIRM GEL |
| 2 | 2 ml | 6 m HEPES 0.5 cc | None | 7.35 at 98.6° F. | 0.10 ml of 40% methylglyoxal - 0.55 millimole (Buffered with 0.3 cc of 6 m, HEPES to pH 7.44 at 98.6° F.) | pH 7.22 at 5 minutes; 2 hours yellow brown gelatin formed at 98.6 F. (at 1 hour 49 minutes last recordable pH 7.35) | GEL |
| 3 | 2 ml | 6 m HEPES 0.3 cc | None | 7.35 at 98.6° F. | 0.20 ml of 40% methylglyoxal buffered with 0.3 cc 6 m HEPES to 7.36 at 98.6° F. | pH 7.07 at 5 minutes; 33 minutes later sudden gelatin formation; yellow brown gelatin | GEL |

TABLE 5

| | A | | | | | A + B + C REACTION MIXTURE | | | | |
|---|---|---|---|---|---|---|---|---|---|---|
| | Bovine Serum Albumin | Buffered B | | pH of A + B | C | pH (98.6° F.) | pH | pH | pH | |
| Sample Number | 30% | pH Adjustment | Protectant | Mixture 5 minutes | Reactant | 15 Minutes | (98.6° F.) 1 Hour | pH (71° F.) 17 Hours | (98.60° F.) 18.5 Hours | FINAL FORM |
| 1 | 2 ml | 6 m HEPES 0.5 cc | 1 millimole L-arginine Hydrochloride | 7.35 | 1 millimole methylglyoxal (0.18 ml of 40% solution) | 6.78 | 6.68; brown liquid | 6.60; brown liquid | 6.52; brown liquid | LIQUID |
| 2 | 2 ml | 6 m HEPES 0.4 ml | 1 millimole L-arginine Hydrochloride | 7.30 | 1 millimole | 6.42 | 6.30; brown liquid | 6.10; brown liquid | 6.09; brown liquid | LIQUID |
| 3 | 2 ml | 6 m HEPES 0.5 ml | 1 millimole D-arginine Hydrochloride | 7.32 | 1 millimole | 6.63 | 6.50; brown liquid | 6.44; brown liquid | 6.32; brown liquid | LIQUID |
| 4 | 2 ml | 6 m HEPES 0.4 ml | 1 millimole D-arginine Hydrochloride | 7.28 | 1 millimole | 6.60 | 6.40; brown liquid | 6.27; brown liquid | 6.23; brown liquid | LIQUID |
| 5 | 2 ml | 6 m HEPES 0.5 ml | None | 7.51 | 1 millimole | Solid yellow gel; last pH estimate 6.91 | Solid yellow gel | Solid yellow gel | Solid yellow gel | SOLID GEL |
| 6 | 2 ml | 6 m HEPES 0.5 ml | 1 millimole glycocyamine | 7.54 | 1 millimole | Yellow, very viscous (soft gel); last pH 6.94 | Yellow, very viscous (soft gel) | Yellow, very viscous (soft gel) | Yellow, very viscous (soft gel) | SOFT GEL |

TABLE 6 pH Adjusted by Titration (NaOH/HCL)

| Sample Number | A<br>Bovine Serum Albumin 30% | B<br>Protectant | C<br>Reactant | REACTION RESULT (A + B + C) | | FINAL FORM |
|---|---|---|---|---|---|---|
| | | | | Immediate pH at 98.6° F. | Observation | |
| 1 | 2 ml BSA | 1 millimole guanidine added to BSA | (1 millimole) 0.18 ml of methylglyoxal 40%; pH adjusted to 7.40 | 5.36 | gel formed immediately on mixing | GEL |
| 2 | 2 ml BSA | No protectant | (1 millimole) 0.18 ml of 40% methylglyoxal; pH adjusted to 7.57 | 5.95 | gel formed rapidly <1 hour | GEL |
| 3 | 2 ml BSA | No protectant | 0.18 ml of 40% methylglyoxal; pH adjusted to 7.30 | 6.12 | at 1 hr. 15 min. pH 6.05, viscous yellow; became solid brown gel overnight | GEL |
| 4 | 2 ml BSA | No protectant | 0.18 ml of 40% methylglyoxal; pH adjusted to 7.07 | 6.25 | initially viscous; gel formed <1 hr. | GEL |
| 5 | 2 ml BSA | 1 millimole of D-arginine Hydrochloride added to BSA; initial pH 5.91; adjusted to pH 7.46 with NaOH/HCL | 0.18 ml of 40% methylglyoxal; pH adjusted to 7.54 | 7.10 | at 1 hr. 5 min. remained brownish, yellow liquid, pH 6.89. Remained liquid overnight; brown with yellow tinge | LIQUID |
| 6 | 2 ml BSA | 1 millimole of L-arginine Hydrochloride added to BSA; pH adjusted to 7.40 with NaOH/HCL | 0.18 ml of 40% methylglyoxal; pH adjusted to 7.29 | 6.15 | remained brownish/yellow liquid; pH 6.00 1 hr. 5 min. later; remained liquid overnight; brown with yellow tinge | LIQUID |
| 7 | 2 ml BSA | 1 millimole L-arginine Hydrochloride not pH adjusted | 0.18 ml of 40% methylglyoxal; pH adjusted to 7.07 | 5.43 | remained brownish/yellow liquid; pH 5.27 1 hr. 5 min later; became viscous overnight; brown with yellow tinge | VISCOUS LIQUID |
| 8 | 2 ml BSA | 1 millimole D-arginine Hydrochloride not pH adjusted | 0.18 ml of 40% methylglyoxal; pH adjusted to 7.30 | 5.62 | remained brownish/yellow liquid; pH 5.44 1 hr. 5 min. later; remained liquid overnight; brown with yellow tinge | LIQUID |

TABLE 7

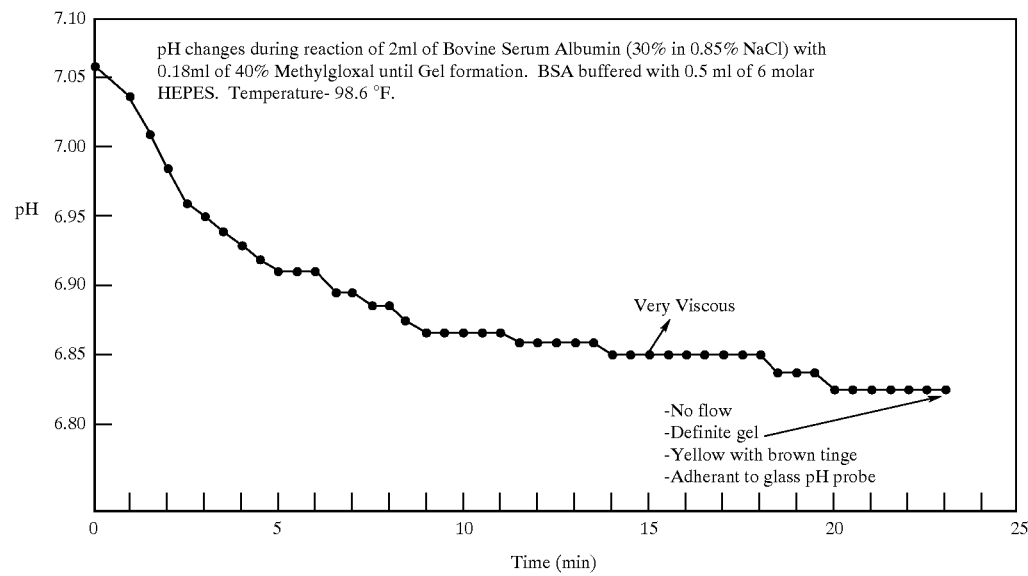

What is claimed is:

1. A method of blocking toxic carbonyl containing compounds and/or dicarbonyl containing compounds in a subject suffering from a condition associated with carbonyl containing compounds and/or dicarbonyl containing compounds by treating blood and/or blood products in a dialysis system for return to the subject comprising administering in the dialysis system a therapeutically effective dose of D-arginine to the subject's blood and/or blood products.

2. The method of claim 1, wherein the D-arginine is administered to blood or blood products, as filterable wash or unremoved treatment, and at molar concentrations of arginine equal to 0.001 mg/100 ml to 60 mg/100 ml of arginine hydrochloride to blood or blood products.

3. The method of claim 1, wherein the D-arginine is administered to blood or blood products, as filterable wash or unremoved treatment, and at molar concentrations of arginine equal to 0.005 mg/100 ml to 50 mg/100 ml of arginine hydrochloride to blood or blood products.

4. The method of claim 1, wherein the D-arginine is administered to blood or blood products, as filterable wash or unremoved treatment, and at molar concentrations of arginine equal to 0.5 mg/100 ml to 40 mg/100 ml of arginine hydrochloride to blood or blood products.

5. A method of treating a subject suffering from diabetes mellitus by treating blood and/or blood products in a dialysis system for return to the subject comprising administering in the dialysis system a therapeutically effective dose of D-arginine to the subject's blood and/or blood products.

6. The method of claim 5, wherein the D-arginine is administered to blood or blood products, as filterable wash or unremoved treatment, and at molar concentrations of arginine equal to 0.001 mg/100 ml to 60 mg/100 ml of arginine hydrochloride to blood or blood products.

7. The method of claim 5, wherein the D-arginine is administered to blood or blood products, as filterable wash or unremoved treatment, and at molar concentrations of arginine equal to 0.005 mg/100 ml to 50 mg/100 ml of arginine hydrochloride to blood or blood products.

8. The method of claim 5, wherein the D-arginine is administered to blood or blood products, as filterable wash or unremoved treatment, and at molar concentrations of arginine equal to 0.5 mg/100 ml to 40 mg/100 ml of arginine hydrochloride to blood or blood products.

* * * * *